United States Patent [19]

Kira et al.

[11] Patent Number: 5,393,664
[45] Date of Patent: Feb. 28, 1995

[54] METHOD OF PREPARING (S)-1-PHENYL-1,3-PROPANEDIOL OR DERIVATIVES THEREOF FROM THEIR RESPECTIVE KETONES

[75] Inventors: Ikuo Kira, Kawasaki; Kazuhiro Watanabe, Tokyo; Eiji Nakanishi, Kawasaki; Hiroshi Ban, Kawasaki; Norimasa Onishi, Kawasaki; Takayuki Suzuki, Kawasaki, all of Japan

[73] Assignee: Ajinomoto Co. Inc., Tokyo, Japan

[21] Appl. No.: 977,007

[22] Filed: Nov. 16, 1992

[30] Foreign Application Priority Data

Nov. 14, 1991 [JP] Japan .................. 3-299131
Feb. 18, 1992 [JP] Japan .................. 4-030782

[51] Int. Cl.$^6$ ........................... C12P 7/22
[52] U.S. Cl. ......................... 435/156; 435/280
[58] Field of Search ..................... 435/280, 156

[56] References Cited

U.S. PATENT DOCUMENTS 4,857,468 10/1989 Kutsuki ..................... 435/280
4,921,798  5/1990 Boaz ....................... 435/146

FOREIGN PATENT DOCUMENTS 0198440 10/1986 European Pat. Off. .
0447938  9/1991 European Pat. Off. .
2832602  8/1979 Germany .
5219984  8/1993 Japan .

OTHER PUBLICATIONS

Christen M. et al, J. Chem. Soc., Chem Commun pp. 264–266 (1988).
Hummel W., Appl Micro Biol Biotechnol 34:15–19 (1990).
Jones, J. B., Tetrahedron 42:3351–3403 (1986).
Hudlicky T. et al, J. Org. Chem 55: 4767–70 (1990).
Chemical Abstracts, vol. 119, No. 25, Dec. 20, 1993, p. 825, AN-269201w.

*Primary Examiner*—Douglas W. Robinson
*Assistant Examiner*—S. Saucier
*Attorney, Agent, or Firm*—Oblon, Spivak, McClelland, Maier & Neustadt

[57] ABSTRACT

(S)-1phenyl-1,3-propanediol or a derivative thereof having high optical purity can be produced simply in high yield, by contacting 1-phenylpropan-3-ol-1-one with a culture of microorganisms, microorganism cells isolated from the culture, or a product obtained by processing the microorganism cells.

32 Claims, No Drawings

METHOD OF PREPARING (S)-1-PHENYL-1,3-PROPANEDIOL OR DERIVATIVES THEREOF FROM THEIR RESPECTIVE KETONES

BACKGROUND OF THE INVENTION

1. Field of the Invention

The present invention relates to a method of preparing (S)-1-phenyl-1,3-propanediol or derivative thereof. (S)-1-phenyl-1,3-propanediol or derivative thereof are useful as raw materials for producing various medicines.

2. Description of the Prior Art

U.S. Pat. No. 4,921,798 reports a method of producing (S)-1-phenyl-1,3-propanediol by asymmetric hydrolysis of a chemically produced racemic ethyl 3-phenyl-3-hydroxypropionate with a lipase to give (S)-3-phenyl-3-hydroxypropionic acid followed by chemical reduction of the acid. However, this method has several drawbacks. The raw materials are expensive and only 50% of them are converted into product. The conversion step is also complicated.

Japanese Chemical Society Abstract 1A438 (March, 1991) reports a method of producing (S)-1-allyl-1,3-propanediol derivatives by subjecting 3-allyl-3-hydroxypropionate ester derivatives to optical resolution with a lipase to give (S)-3-allyl-3-hydroxypropionate ester derivatives followed by deesterification and reduction. However, this method produces products in low yield and includes a step that is complicated. Thus, there remains a need for a simplified and inexpensive method for preparing (S)-1-phenyl-1,3-propanediol and derivatives thereof.

SUMMARY OF THE INVENTION

Accordingly, it is an object of the present invention to provide an inexpensive and simple method of producing (S)-1-phenyl-1,3-propanediol or derivatives thereof having high optical purity.

This and other objects, which will become apparent during the following detailed description, have been achieved by the inventors' discovery of an inexpensive and simple method of producing (S)-1-phenyl-1,3-propanediol or derivatives thereof having a high optical purity, of from 75 to 100% e.e., through asymmetric reduction of 1-phenylpropan-3-ol-1-one or derivatives thereof via a microorganism. (S)-1-phenyl-1,3-propanediol or derivatives thereof are thereby produced.

DETAILED DESCRIPTION OF THE PREFERRED EMBODIMENTS

Specifically, the present invention provides a method of preparing (S)-1-phenyl-1,3-propanediol or derivatives thereof utilizing a culture of microorganisms capable of asymmetrically reducing 1-phenylpropan-3-ol-1-one or a derivative thereof, represented by the following general formula (1), into (S)-1-phenyl-1,3-propanediol or a derivative thereof, represented by the following general formula (2). 1-phenylpropan-3-ol-1-one or a derivative thereof as represented by formula (1) is treated with a culture of the microorganism or to a solution containing isolated microorganism cells or any cell fraction or extract capable of converting (1) to (2). The starting 1-phenylpropan-3-ol-1-one compounds have the structure represented by formula (1)

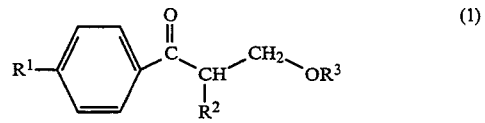

where $R^1$ represents a hydrogen atom, a halogen atom or a $C_{1-4}$-alkyl group; $R^2$ represents a hydrogen atom or a $C_{1-4}$-alkyl group; and $R^3$ represents a hydrogen atom or a $C_{1-4}$-acyl group. The final products of the present method have the structure represented by formula (2)

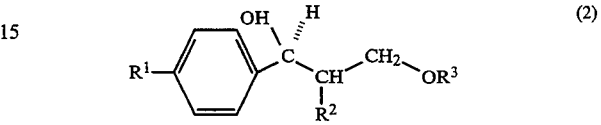

where $R^1$ represents a hydrogen atom, a halogen atom or a $C_{1-4}$-alkyl group; $R^2$ represents a hydrogen atom or a $C_{1-4}$-alkyl group; and $R^3$ represents a hydrogen atom or a $C_{1-4}$-acyl group.

The starting 1-phenylpropan-3-ol-1-one compounds can be synthesized by condensing acetophenone and formaldehyde as described by Mekhtieu et al (Dokl. Akad. Nouk. Azerb. SSR (1971), vol. 27, p. 38).

The microorganisms to be used in the present invention may be any microorganism capable of asymmetrically reducing 1-phenylpropan-3-ol-1-one or derivative thereof into (S)-1-phenyl-1,3-propanediol or derivative thereof. The following microorganisms can be used:

Arthrobacter paraffineus ATCC15591
Aureobacterium testaceum JCM1354
Clavibacter michiganense ATCC7429
Enterobacter cloacae IFO3320
Flavobacterium esteraromaticum IFO3751
Nocardia asteroides ATCC3318
Rhodococcus erythropolis ATCC4277
Serratia marcescens ATCC14226
Candida cantarellii IFO1261
Citeromyces matritensis IFO0651
Cryptococcus albidus IFO0610 (FERM BP-3957)
Cryptococcus albidus IFO0612
Hansenula mrakii IFO0895
Hansenula mrakii IFO0896 (FERM BP-3958)
Kloeckera javanica IFO0669
Aureobasidium pullulans IFO6353
Curvularia trifoli IFO7276
Gelasinospora longispora IFO8658
Monascus araneosus IFO4482
Mucor javanicus IFO4570
Rhizopus delemar IFO4801
Sclerotium bataticola CBS271.34 (FERM BP-3956)
Sclerotium bataticola CBS459.70
Septoria cucurbitacearum IFO7479
Westerdykella multispora IFO7895

These microorganisms may be either wild type or mutants. In addition, recombinant strains derived using genetic means such as cell fusion or genetic engineering may also be used.

The medium used for cultivating the microorganisms for use in the present invention can be any medium on which the microorganisms will grow. For example, an ordinary liquid nutrient medium containing carbon sources, nitrogen sources, inorganic salts and organic nutrients can be used.

Carbon sources in the medium may be any carbon source which can be assimilated by the above-mentioned microorganisms. These include saccharides such as glucose, fructose, sucrose and dextrin; alcohols such as sorbitol, ethanol and glycerol; organic acids such as fumaric acid, citric acid, acetic acid and propionic acid and their salts; hydrocarbons such as paraffin; and mixtures thereof.

Nitrogen sources which may be used include, for example, inorganic ammonium salts such as ammonium chloride; organic acid ammonium salts such as ammonium fumarate and ammonium citrate; nitrates such as sodium nitrate and potassium nitrate; organic nitrogen compounds such as peptone, yeast extract, broth and corn steep liquor; and mixtures thereof.

In addition, the medium for use in the present invention may further contain other nutrient sources which are used in ordinary cultivation, such as inorganic salts, minor metal salts and vitamins. If desired, the medium may also contain compounds for promoting propagation of the microorganisms, compounds for elevating the microorganisms' efficiency for producing the product compounds of the present invention, as well as substances effective for maintaining a suitable pH value in the medium.

Cultivation of the microorganisms in the medium is effected anaerobically or aerobically under conditions suitable for the growth of the microorganisms, for example, at a pH value of from 3 to 9.5, preferably of from 4 to 8, and at a medium temperature of from 20° to 45° C. preferably of from 25° to 37° C., for a period of approximately from 5 to 120 hours, preferably from 12 to 72 hours.

1-phenylpropan-3-ol-1-one or a derivative thereof may be added to a culture of the microorganisms. Alternatively, microorganism cells may be isolated from a culture of the microorganisms by centrifugation or the like; suspended in water, a buffer or the like, directly or after washing; and 1-phenylpropan-3-ol-1-one or a derivative thereof may be added to the resulting suspension. During the reaction, it may be desirable to add a carbon source such as glucose, fructose or sucrose to the medium as an energy source.

Products of the microorganisms cells also usable in the present invention include fragmented cells, acetone-processed cells, freeze-dried cells, as well as cells fixed by known methods such as a polyacrylamide gel method, carrageenan method or arginic acid gel method. In addition, products of the microorganism cells which also can be used include cell extracts and the enzyme which catalyzes the asymmetric reduction. This enzyme can be isolated from the cell extracts. If the isolated enzyme is used, it is preferred to add the co-enzymes NADH or NADPH to the reaction mixture.

In carrying out the method of the present invention, 1-phenylpropan-3-ol-1-one or a derivative thereof may be added to the reaction system, directly or after being dissolved in water or in an inert organic solvent or after being dispersed in a surfactant or the like. 1-phenylpropan-3-ol-1-one or a derivative thereof can be added all at once before the reaction or incrementally as aliquots during the course of the reaction. Various concentrations of 1-phenylpropan-3-ol-1-one can be added, but the concentration is preferably approximately of from 0.1 to 10% by weight/volume, most preferably 1 to 5% by weight/volume based on the total volume of the culture medium.

The reaction is effected with stirring or under static condition, at a pH value of from 3 to 9, preferably of from 5 to 8, and at a temperature of from 10° to 60° C. preferably of from 20° to 40° C. The reaction is carried out for approximately from 1 to 120 hours, whereupon (S)-1-phenyl-1,3-propanediol or a derivative thereof having a high optical purity is formed and accumulated in the reaction liquid.

Collection of the (S)-1-phenyl-1,3-propanediol or a derivative thereof is effected with ease directly from the reaction mixture, or after the cells are separated therefrom. The reaction mixture is subjected to any ordinary purification method such as extraction with an organic solvent, distillation or column chromatography.

The following examples are provided to illustrate specific embodiments of the present invention. The examples are included for illustrative purposes only and are not intended to limit the scope of the present invention.

EXAMPLES

Determination of the absolute configuration, optical purity and reaction yield of 1-phenyl-1,3-propanediol or a derivative thereof in the examples was determined by high pressure liquid chromatography (column: Chiral Cell OB, manufactured by Daisel Chemical Co., eluent: hexane/2-propanol (8/2), flow rate: 0.7 ml/min, detection: UV 210 nm). The reaction yield represents the mole percentage of (S)-1-phenyl-1,3-propanediol produced per mole of 1-phenylpropan-3-ol-1-one added as starting material.

EXAMPLE 1

3 ml of medium (pH 7.0) containing 2.0% glucose, 0.5% $(NH_4)_2SO_4$, 0.3% $K_2PO_4$, 0.1% $KH_2PO_4$, 0.05% $MgSO_4.7H_2O$, 0.001% $FeSO_4.7H_2O$, 0.001% $MnSO_4.4H_2O$, 1.0% yeast extract and 1.0% polypeptone was placed in test tubes and sterilized under heat. Cells of the microorganisms shown in Table 1, which had been previously cultivated in a bouillon-agar medium at 30° C. for 24 hours, were inoculated onto the medium via a platinum loop and cultivated therein at 30° C. for 24 to 48 hours by shaking culture. Next, 3 mg 1-phenylpropan-3-ol-1-one and 15 mg glucose were added to the culture and further reacted for 24 hours at 30° C. with shaking. Subsequently, the reaction mixture was diluted with ethanol, the cells were removed from the reaction mixture by centrifugation, and the resulting supernatant was subjected to high pressure liquid chromatography. The absolute liquid configuration, optical purity and reaction yield of 1-phenyl-1,3-propanediol were measured. The results obtained are shown in Table 1 below.

TABLE 1

| | 1-Phenyl-1,3-propanediol | | |
|---|---|---|---|
| Microorganisms | Reaction Yield (%) | Absolute Configuration | Optical Purity (% e.e.) |
| Arthrobacter paraffineus ATCC15591 | 16.9 | S | 95 |
| Aureobacterium testaceum JCM1354 | 10.1 | S | 100 |
| Clavibacter michiganense ATCC7429 | 17.5 | S | 92 |
| Enterobacter cloacae IFO3320 | 24.2 | S | 94 |
| Flavobacterium esteraromaticum IFO3751 | 10.0 | S | 92 |
| Nocardia asteroides ATCC3318 | 18.8 | S | 89 |
| Rhodococcus erythropolis | 27.4 | S | 86 |

TABLE 1-continued

| | 1-Phenyl-1,3-propanediol | | |
|---|---|---|---|
| Microorganisms | Reaction Yield (%) | Absolute Configuration | Optical Purity (% e.e.) |
| ATCC4277 | | | |
| Serratia marcescens ATCC14226 | 11.5 | S | 81 |
| Candida cantarellii IFO1261 | 56.6 | S | 86 |
| Citeromyces matritensis IFO0651 | 12.2 | S | 92 |
| Cryptococcus albidus IFO0610 | 90.0 | S | 100 |
| Cryptococcus albidus IFO0612 | 90.0 | S | 100 |
| Hansenula mrakii IFO0895 | 94.0 | S | 100 |
| Hansenula mrakii IFO0896 | 94.0 | S | 100 |
| Kloeckera javanica IFO0669 | 37.9 | S | 100 |
| Aureobasidium pullulans IFO6353 | 27.1 | S | 100 |
| Curvularia trifoli IFO7276 | 18.1 | S | 84 |
| Gelasinospora longispora IFO8658 | 14.1 | S | 83 |
| Monascus araneosus IFO4482 | 25.2 | S | 92 |
| Mucor javaninicus IFO4570 | 21.2 | S | 93 |
| Rhizopus delemar IFO4801 | 25.3 | S | 100 |
| Sclerotium bataticola CBS271.34 | 82.7 | S | 96 |
| Sclerotium bataticola CBS459.70 | 82.7 | S | 96 |
| Septoria cucurbitacearum IFO7479 | 20.0 | S | 100 |
| Westerdykella multispora IFO7895 | 24.6 | S | 83 |

EXAMPLE 2

50 ml of medium having the same composition as Example 1 was placed in 500 ml-capacity Sakaguchi flasks and sterilized under heat. One platinum loop containing cells of Hansenula mrakii IFO0896 was inoculated and cultivated therein at 30° C. for 24 hours by shaking culture. Next, 0.5 g 1-phenylpropan-3-ol-1-one and 2.5 g glucose were added to the culture and further reacted at 30° C. for 72 hours with shaking. After the reaction, the absolute configuration, optical purity and reaction yield of 1-phenyl-1,3-propanediol were determined. The absolute configuration was (S)-form, the optical purity was 100% and the reaction yield was 88.3%.

EXAMPLE 3

1.0 liter of medium having the same composition as Example 1 was placed in 2 liter-capacity mini jar fermenters and sterilized under heat, and 80 ml of a culture of Hansenula mrakii IFO0896, obtained by previously cultivating in the same medium at 30° C. for 24 hours by shaking culture, was inoculated and cultivated therein at 30° C. for 24 hours with an air flow rate of 1 L of air per 1 L of fermentation medium per minute (1 vvm) and a stirring rate of 500 rpm. After the cultivation, the cells were collected by centrifugation and washed with 200 mM phosphate buffer (pH 7.5) in an amount equal to the amount of culture. These cells were then suspended in 500 ml of the same buffer. 25 g glucose and 2.5 g 1-phenylpropan-3-ol-1-one were added to this suspension and reacted with continuous air flow and stirring at 30° C. After 12 hours and 24 hours, 2.5 g 1-phenylpropan-3-ol-1-one was added to the reaction mixture. The reaction was left stirring for a total of 48 hours. After the reaction, the absolute configuration, optical purity and reaction yield of 1-phenyl-1,3-propanediol were determined. The absolute configuration was (S)-form, the optical purity was 100% and the reaction yield was 89.6%.

Next, the reaction mixture was filtered through an ultrafilter membrane, and the resulting filtrate was extracted two times each with 500 ml of a mixed solvent system containing toluene/isopropanol. After concentrating under reduced pressure, crystallizing and drying, 5.4 g of crystalline (S)-1-phenyl-1,3-propanediol was obtained.

EXAMPLE 4

50 ml of medium having the same composition as Example 1 was placed in 500 ml-capacity Sakaguchi flasks and sterilized under heat. One platinum loop of cells of Hansenula mrakii IFO0896 was inoculated and cultivated therein at 30° C. for 24 hours by shaking culture. After the cultivation, the cells were collected by centrifugation and washed with 50 mM tris-hydrochloride buffer (pH 7.5) in an amount equal to the amount of culture. One ml of the same buffer was added to 2.68 g of the wet cells thus obtained to form a cell suspension. The cell suspension was ground in a mortar, 4 ml of the same buffer was added thereto, and the cell debris was removed by centrifugation to obtain a supernatant of a cell-free extract.

Next, 0.5 ml of a coenzyme solution (NADPH 18.1 mg/ml in tris-hydrochloride buffer) and 1.5 mg 1-phenylpropan-3-ol-1-one were added to 0.5 ml of the cell-free extract described above and reacted at 30° C. for 28 hours. After the reaction, the absolute configuration, optical purity and reaction yield of the 1-phenyl-1,3-propanediol were determined. The absolute configuration was (S)-form, the optical purity was 100% and the reaction yield was 76.5%.

EXAMPLE 5

5 ml of medium having the same composition as Example 1 was placed into test tubes and sterilized under heat. Cells of microorganisms as shown in Table 2, which had previously been cultivated in a bouillon-agar medium at 30° C. for 24 hours, were inoculated via a platinum loop and cultivated therein at 30° C. for a period of from 24 to 48 hours by shaking culture. After the cultivation, the cells were collected by centrifugation, washed with 5 ml of 200 mM phosphate buffer (pH 7.5) and suspended in 5 ml of the same buffer. 10 mg 1-(4-chlorophenyl)-3-hydroxypropan-1-one and 250 mg glucose were added to the suspension and reacted at 30° C. for 24 hours with shaking. After the reaction, the reaction mixture was diluted with ethanol, the cells were removed therefrom by centrifugation, and the resulting supernatant was subjected to high pressure liquid chromatography to determine the absolute configuration, optical purity and reaction yield of 1-(4-chlorophenyl)-1,3-propanediol. The results obtained are shown in Table 2.

TABLE 2

| | 1-(4-Chlorophenyl)-1,3-propanediol | | |
|---|---|---|---|
| Microorganisms | Reaction Yield (%) | Absolute Configuration | Optical Purity (% e.e.) |
| Cryptococcus albidus IFO0610 | 58 | S | 100 |
| Hansenula mrakii IFO0896 | 95 | S | 100 |
| Sclerotium bataticola CBS271.34 | 90 | S | 96 |

EXAMPLE 6

5 ml of medium having the same composition as Example 1 was placed into test tubes and sterilized under heat. Cells of the microorganisms as shown in Table 3, which had previously been cultivated in a bouillon-agar medium at 30° C. for 24 hours, were inoculated via a platinum loop and cultivated therein at 30° C. for a period of from 24 to 48 hours by shaking culture. Next, the cells were washed in the same manner as in Example 5. 10 mg 3-hydroxy-1-(4-methylphenyl)propan-1-one and 250 mg glucose were added to the suspension and reacted at 30° C. for 24 hours with shaking. After the reaction, the reaction mixture was treated in the same manner as in Example 5 to determine the absolute configuration, optical purity and reaction yield of 1-(4-methylphenyl)-1,3-propanediol. The results obtained are shown in Table 3.

TABLE 3

| Microorganisms | 1-(4-Chlorophenyl)-1,3-propanediol | | |
|---|---|---|---|
| | Reaction Yield (%) | Absolute Configuration | Optical Purity (% e.e.) |
| Cryptococcus albidus IFO0610 | 63 | S | 100 |
| Hansenula mrakii IFO0896 | 65 | S | 100 |
| Sclerotium bataticola CBS271.34 | 75 | S | 96 |

EXAMPLE 7

5 ml of medium having the same composition as Example 1 was placed into test tubes and sterilized under heat. Cells of the microorganisms as shown in Table 4, which had previously been cultivated in a bouillon-agar medium at 30° C. for 24 hours, were inoculated via a platinum loop and cultivated therein at 30° C. for a period of from 24 to 48 hours by shaking culture. Next, the cells were washed in the same manner as in Example 5. 10 mg 1-phenyl-3-acetoxypropan-1-one and 250 mg glucose were added to the suspension and reacted at 30° C. for 24 hours with shaking. After the reaction, the reaction mixture was treated in the same manner as in Example 5 to determine the absolute configuration, optical purity and reaction yield of 3-acetoxyl-1-phenyl-1-propanol. The results obtained are shown in Table 4.

TABLE 4

| Microorganisms | Reaction Yield (%) | Absolute Configuration | Optical Purity (% e.e.) |
|---|---|---|---|
| Cryptococcus albidus IFO0610 | 63 | S | 100 |
| Hansenula mrakii IFO0896 | 95 | S | 100 |
| Sclerotium bataticola CBS271.34 | 90 | S | 96 |

EXAMPLE 8

5 ml of medium having the same composition as Example 1 was placed into test tubes and sterilized under heat. Cells of the microorganisms as shown in Table 5 below, which had previously been cultivated in a bouillon-agar medium at 30° C. for 24 hours, were inoculated via a platinum loop and cultivated therein at 30° C. for a period of from 24 to 48 hours by shaking culture. Next, the cells were washed in the same manner as in Example 5. 10 mg 3-hydroxy-(R,S)-2-methyl-1-phenyl-propan-1-one and 250 mg glucose were added to the suspension and reacted at 30° C. for 24 hours with shaking. After which the reaction mixture was treated in the same manner as in Example 5 to determine the absolute configuration, optical purity and reaction yield of 2-methyl-1-phenyl-1,3-propanediol. The obtained product was diastomeric at the 2-position. The results obtained are shown in Table 5.

TABLE 5

| Microorganisms | Reaction Yield (%) | Absolute Configuration | Optical Purity (% e.e.) |
|---|---|---|---|
| Cryptococcus albidus IFO0610 | 30 | S | 100 |
| Hansenula mrakii IFO0896 | 8 | S | 100 |
| Sclerotium bataticola CBS271.34 | 55 | S | 96 |

EXAMPLE 9

50 ml of medium having the same composition as Example 1 was placed into 500 ml-capacity Sakaguchi flasks and sterilized under heat. One platinum loop of cells of Hansenula mrakii IFO0896, which had previously been cultivated in a bouillon-agar medium at 30° C. for 24 hours, was inoculated and cultivated therein at 30° C. for 24 hours by shaking culture. Next, 0.5 g 1-(4-chlorophenyl)-3-hydroxypropan-1-one and 2.5 g glucose were added to the culture and reacted at 30° C. for 72 hours with shaking. After the reaction, the absolute configuration, optical purity and reaction yield of 1-(4-chlorophenyl)-1,3-propanediol were measured. The absolute configuration was (S)-form; the optical purity was 100%; and the reaction yield was 88.3%.

EXAMPLE 10

1.0 liter of medium having the same composition as shown in Example 1 was placed into 2 liter-capacity mini-jar fermenters and sterilized under heat. 80 ml of a culture of Hansenula mrakii IFO0896, which had previously been cultivated in the same medium at 30° C. for 24 hours, was inoculated and cultivated therein at 30° C. for 24 hours with an air flow rate of one vvm and a stirring rate of 500 rpm. After the cultivation, the cells were collected from the culture by centrifugation and washed with 200 mM phosphate buffer (pH 7.5) in an amount equal to the amount of culture, and then suspended in 500 ml of the same buffer. 25 g glucose and 2.5 g 1-(4-chlorophenyl)-3-hydroxy-propan-1-one were added to the suspension and reacted with continuous air flow and stirring at 30° C. After 12 hours and 24 hours, 2.5 g 1-(4-chlorophenyl)-1,3-propanediol was added to the reaction mixture. The total reaction time was 48 hours. After the reaction, the absolute configuration, optical purity and reaction yield of 1(4-chlorophenyl)-1,3-propanediol were measured. The absolute configuration was (S)-form; the optical purity was 100%; and the reaction yield was 89.6%.

Next, the reaction mixture was filtered through an ultrafilter membrane, and the resulting filtrate was extracted two times each with 500 ml of a mixed solvent of toluene/isopropanol. After concentration under reduced pressure, crystallization and drying, 5.8 g of crystalline of (S)-(4-chlorophenyl)-1,3-propanediol was obtained.

EXAMPLE 11

50 ml of medium having the same composition as Example 1 was placed into 500 ml-capacity Sakaguchi flasks and sterilized under heat. One platinum loop of cells of Hansenula mrakii IFO0896 was inoculated and cultivated therein at 30° C. for 24 hours by shaking culture. After the cultivation, the cells were collected by centrifugation and washed with 50 mM tris-hydrochloride buffer (pH 7.5) in an amount equal to that of the culture. One ml of the same buffer was added to 2.68 g of the wet cells thus obtained to form a cell suspension. The cell suspension was ground in a mortar, 4 ml of the same buffer was added thereto, and the cell debris were removed by centrifugation to obtain a supernatant of a cell-free extract.

Next, 0.5 ml of a co-enzyme solution (NADPH 18.1 mg/ml in tris-hydrochloride buffer) and 1.5 mg 1-(4-chlorophenyl)-3-hydroxypropan-1-one were added to 0.5 ml of the thus obtained cell-free extract and reacted at 30° C. for 28 hours. After the reaction, the absolute configuration, optical purity and reaction yield of 1-(4-chlorophenyl)-1,3-propanediol were determined. The absolute configuration was (S)-form, the optical purity was 100% and the reaction yield was 75%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for preparing a (S)-1-phenyl-1,3-propanediol compound of formula (2), comprising contacting a compound of formula (1)

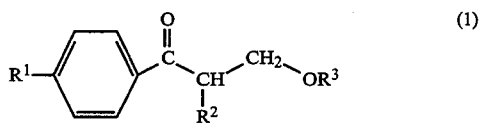

wherein a $R^1$ is a hydrogen atom, a halogen atom, or a $C_{1-4}$ alkyl group; $R^2$ is a hydrogen atom or a $C_{1-4}$-alkyl group; and $R^3$ is a hydrogen atom or a $C_{1-4}$ acyl group, with one member selected from the group consisting of:
   (a) a culture of a microorganism capable of asymmetrically reducing said compound of formula (1),
   (b) cells isolated from a culture of a microorganism capable of asymmetrically reducing said compound of formula (1), and
   (c) a cell product obtained from a microorganism capable of asymmetrically reducing said compound of formula (1);
for a time sufficient to produce said (S)-1-phenyl-1,3-propanediol compound of formula (2)

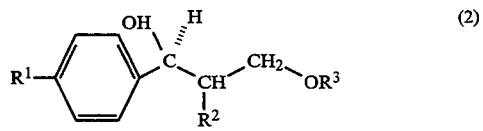

wherein $R^1$, $R^2$ and $R^3$ are defined as above;
and recovering said compound of formula (2); wherein said microorganism is selected from the group consisting of
*Arthrobacter paraffineus,*
*Aureobacterium testaceum,*
*Clavibacter michiganense,*
*Enterobacter cloacae,*
*Flavobacterium esteraromaticum,*
*Nocardia asteroides,*
*Rhodococcus erythropolis,*
*Serratia marcescens,*
*Candida cantarellii,*
*Citeromyces matritensis,*
*Cryptococcus albidus,*
*Hansenula mrakii,*
*Kloeckera javanica,*
*Aureobasidium pullulans,*
*Curvularia trifolii,*
*Gelasinospora longispora,*
*Monascus araneosus,*
*Mucor javanicus,*
*Rhizopus delemar,*
*Sclerotium bataticola,*
*Septoria cucurbitacearum* and
*Westerdykella multispora.*

2. The method of claim 1, wherein said microorganism is *Arthrobacter paraffineus.*

3. The method of claim 1, wherein said microorganism is *Aureobacterium testaceum.*

4. The method of claim 1, wherein said microorganism is *Clavibacter michiganense.*

5. The method of claim 1, wherein said microorganism is *Enterobacter cloacae.*

6. The method of claim 1, wherein said microorganism is *Flavobacterium esteraromaticum.*

7. The method of claim 1, wherein said microorganism is *Nocardia asteroides.*

8. The method of claim 1, wherein said microorganism is *Rhodococcus erythropolis.*

9. The method of claim 1, wherein said microorganism is *Serratia marcescens.*

10. The method of claim 1, wherein said microorganism is *Candida cantarellii.*

11. The method of claim 1, wherein said microorganism is *Citeromyces matritensis.*

12. The method of claim 1, wherein said microorganism is *Cryptococcus albidus.*

13. The method of claim 1, wherein said microorganism is *Hansenula mrakii.*

14. The method of claim 1, wherein said microorganism is *Kloeckera javanica.*

15. The method of claim 1, wherein said microorganism is *Aureobasidium pullulans.*

16. The method of claim 1, wherein said microorganism is *Curvularia trifolii.*

17. The method of claim 1, wherein said microorganism is *Gelasinospora longispora.*

18. The method of claim 1, wherein said microorganism is *Monascus araneosus.*

19. The method of claim 1, wherein said microorganism is *Mucor javanicus.*

20. The method of claim 1, wherein said microorganism is *Rhizopus delemar.*

21. The method of claim 1, wherein said microorganism is *Sclerotium bataticola.*

22. The method of claim 1, wherein said microorganism is *Septoria cucurbitacearum.*

23. The method of claim 1, wherein said microorganism is *Westerdykella multispora.*

24. The method of claim 1, wherein said microorganism is cultivated in a medium which is at a pH value from 3 to 9.5.

25. The method of claim 1, wherein the pH value of the medium is from 4 to 8.

26. The method of claim 1, wherein said microorganism is cultivated in a media at a temperature range from 20° to 45° C.

27. The method of claim 26, wherein said temperature is from 25° to 37° C.

28. The method of claim 1, wherein said contacting is carried out for a time of from 5 to 120 hours.

29. The method of claim 7, wherein said time is from 12 to 72 hours.

30. The method of claim 1, wherein said cell product is fragmented cells, acetone-processed cells, freeze-dried cells, cells fixed by polyacrylamide gel method, cells fixed by carrageenan method or cells fixed by arginic acid gel method.

31. The method of claim 1, wherein said 1-phenylpropan-3-ol-1-one is present in an amount from 0.1 to 10% by weight/volume based on the total volume of the culture medium, during said contacting.

32. The method of claim 1, wherein said 1-phenylpropan-3-ol-1-one is present in an amount from 1 to 5% by weight/volume based on the total volume of the culture medium, during said contacting.

* * * * *

UNITED STATES PATENT AND TRADEMARK OFFICE
CERTIFICATE OF CORRECTION

PATENT NO. : 5,393,664
DATED : February 28, 1995
INVENTOR(S) : Ikuo Kira, et. al.

It is certified that error appears in the above-indentified patent and that said Letters Patent is hereby corrected as shown below:

Column 4, line 35, delete "$K_2PO_4$" and insert --$K_2HPO_4$--.

Column 5, line 29, delete "Hansenula mrakii" and insert --*Hansenula mrakii*--.

Column 9, line 34, delete "$C_{1-4}$ alkyl" and insert --$C_{1-4}$-alkyl--.

Signed and Sealed this

Twelfth Day of March, 1996

BRUCE LEHMAN

*Attest:*

*Attesting Officer*     *Commissioner of Patents and Trademarks*